United States Patent [19]

Drago et al.

[11] 4,417,077

[45] Nov. 22, 1983

[54] HETEROGENEOUS ANIONIC TRANSITION METAL CATALYSTS

[75] Inventors: Russell S. Drago, Champaign, Ill.; Anton El A'mma, Bensalem, Pa.

[73] Assignee: University of Illinois Foundation, Urbana, Ill.

[21] Appl. No.: 342,689

[22] Filed: Jan. 26, 1982

Related U.S. Application Data

[60] Division of Ser. No. 192,793, Oct. 1, 1980, Pat. No. 4,328,125, which is a continuation of Ser. No. 38,551, May 14, 1979, abandoned.

[51] Int. Cl.$^3$ ............................................. C07C 45/50
[52] U.S. Cl. ..................................... 568/454; 568/909
[58] Field of Search ................. 568/454, 909; 252/426

[56] References Cited

U.S. PATENT DOCUMENTS

| | | | |
|---|---|---|---|
| 3,725,305 | 4/1973 | Wilkinson | 568/454 |
| 4,013,583 | 3/1977 | Knifton | 568/454 |
| 4,317,936 | 3/1982 | Kim et al. | 568/454 |
| 4,328,125 | 5/1982 | Drago et al. | 252/426 |

*Primary Examiner*—Werren B. Lone
*Attorney, Agent, or Firm*—George M. Yahwak

[57] ABSTRACT

Novel heterogeneous catalysts consist essentially of an anion exchange resin to which is bound ionically an anionic metal carbonyl species having the general formula $M_n(CO)_m(X)_p{}^{z-}$ where M is a transition metal such as for example rhodium, cobalt, ruthenium, osmium, iridium, or iron; X is an anion, for example halide, hydride, or alkyl; n ranges from 1 to 12; m ranges from 1 to 34; p ranges from 0 to $2n+1$; and z is an integer charge ranging from 1 to 5. The catalyst in which M is rhodium, $m=2$, $p=2$, $n=1$, and $z=1$ is highly effective for the carbonylation of alcohols to acids and esters. Many of these anionic species have utility in the hydroformylation of olefins.

6 Claims, No Drawings

HETEROGENEOUS ANIONIC TRANSITION METAL CATALYSTS

The Government has rights in this invention pursuant to Contract No. N00014-78-C-0245 awarded by the Department of the Navy.

This application is a divisional of our prior U.S. application, Ser. No. 192,793, filed on Oct. 1, 1980, now U.S. Pat. No. 4,328,125, which is in turn a continuation of our prior U.S. application, Ser. No. 038,551, filed May 14, 1979, now abandoned.

This invention relates to heterogeneous catalyst compositions formed by transition metal anions, to methods of preparing such catalysts, and to carbonylation and hydroformylation reactions that can be effected with such catalysts. More specifically, this invention is concerned with novel heterogeneous anionic transition metal catalysts for the carbonylation of alcohols for the production of carboxylic acids and esters thereof. Additionally, this invention is concerned with the application of these novel catalysts for the hydroformylation of olefins.

The use of heterogeneous neutral and cationic metal catalysts for carbonylation and hydroformylation reactions is well known in the art. For example, Wilkinson, U.S. Pat. No. 3,725,305 discloses a catalyst consisting essentially of a cationic transition metal complex adsorbed on a resin, which catalyst is useful for carbonylation of alcohols, hydroformylation reactions, and the like Schultz, U.S. Pat. No. 3,717,670 discloses a rhodium catalyst promoted with a second metal which is dispersed on a porous, inert carrier such as pumice, alumina, silica, and the like. The catalyst is useful for the carbonylation of alcohols.

Other transition metal catalysts adsorbed upon solid supports are disclosed in Rony, et al., U.S. Pat. No. 3,855,307 and Hwang, U.S. Pat. No. 4,101,450.

Certain disadvantages present in the catalysts described in the prior art include poor selectivity, low reactivity, poor stability, and poor resistance of the transition metal component of the catalyst to leaching into the reaction medium.

Accordingly, it is an object of this invention to provide a heterogeneous transition metal catalyst that eliminates or minimizes the disadvantages of prior art catalysts.

It is another object of this invention to provide a catalyst consisting essentially of an anionic species containing the transition metal which is ionically bound to an anion exchange resin.

It is still another object of this invention to provide an improved process for the carbonylation of alcohols to produce carboxylic acids and esters thereof, utilizing the inventive catalyst compositions.

It is a further object of this invention to provide an improved process for the hydroformylation of olefins, utilizing the inventive catalyst compositions.

These and other objects will be found in the following detailed description of the invention.

In accordance with this invention, heterogeneous anionic metal catalysts are prepared by treating a resin containing a polymeric quaternary ammonium salt with a neutral transition metal carbonyl compound as illustrated by the following equation:

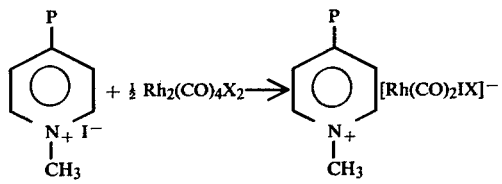

where P represents a polymeric hydrocarbon backbone and X is Cl or I. Most metals from the transition element block can be employed in this reaction, for example rhodium, cobalt, ruthenium, osmium, iridium, and iron. The transition metal carbonyl compound is converted to the anion having the general formula

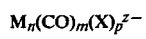

where M is the transition metal; X is an anion such as halide, hydride, or alkyl; n ranges from 1 to 12; m ranges from 1 to 34; p ranges from 0 to 2n+1; and z is an integer charge ranging from 1 to 5. The anion so formed becomes ionically bound to the cationic polymer.

The transition metal carbonyl-containing anionic species can also be preformed in solution and anion exchanged onto the resin. It is also possible to exchange other transition metal species onto the resin and then convert them to carbonyl-containing anions.

Suitable resins for providing polymeric quaternary salt sites include polyvinyl pyridines and polystyrene bound pyridines such as

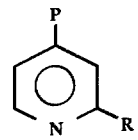

where P represents a polymeric backbone such as polystyrene, and R is hydrogen or a lower alkyl group. The quaternary ammonium cation is readily formed by reaction with and alkyl halide such as $CH_3I$. Polymer bound amines and congeners of nitrogen can be similarly treated.

Commercially available anion exchange resins can be used to advantage in the practice of this invention. Examples of such resins are the Amberlite 1RA-400 or Dowex 1-X3 resins which can be illustrated by the formula:

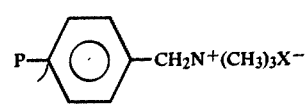

where P represents a polymeric backbone such as polystyrene, and X is an anion such as Cl, I, or acetate.

The invention can be more readily understood and illustrated by reference to the following procedures and examples.

EXAMPLE 1

Preparation of polystyrene bound methylpyridinium iodide.

Polystyrene bound pyridine (10% cross-linked, 5 mole % substituted) in amount of 1.0 g was added to a stirred solution of Spectrograde benzene (20 ml) and iodomethane (5.0 ml) in a 50 ml round bottom flask. The mixture was refluxed for about 23 hours, after which the yellow beads formed were collected by suction and air-dried. The quaternary ammonium iodide salt forms according to the following equation:

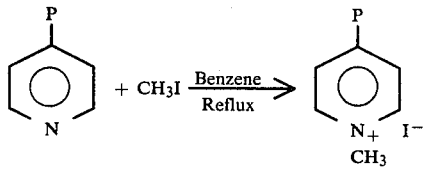

EXAMPLE 2

Reaction of polystyrene bound methylpyridinium iodide with di-μ-chlorotatracarbonyldirhodium.

Polystyrene bound methylpyridinium iodide (1.0 g) and $Rh_2(CO)_4Cl_2$ (100 mg) were stirred in benzene (25 ml) at room temperature for one hour under argon. The beads were isolated by suction and air-dried.

A sample of the beads formed was milled in a Wig-L-Bug amalgamator. Six mg of the ground resin were then dispersed in KBr (85 mg) and a pellet was made for an infrared study of the polymer in the carbonyl C-O stretching region. Two strong absorption bands were observed at 1981 cm$^{-1}$ and 2065 cm$^{-1}$, coinciding with those recorded for $[Rh(CO)_2I_2]^-$ in solution. This indicates the presence of the identical anion which is ionically bound to the immobilized methylpyridinium counter cation, as illustrated by the following equation:

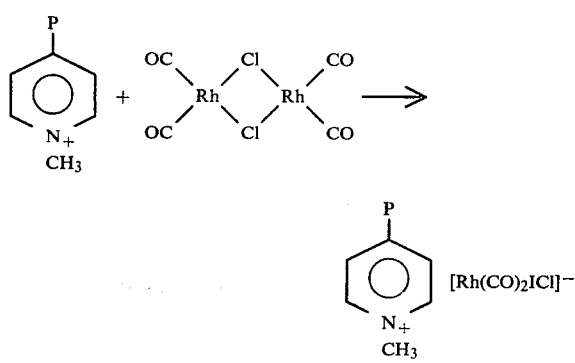

EXAMPLE 3

Catalytic carbonylation of methanol with polystyrene bound methylpyridinium-dichloro-dicarbonylrhodate A solution of 3:7 methanol-benzene by volume (50 ml) was added to a 500 ml Parr glass pressure bottle together with 0.5 g of the indicated catalyst. Iodomethane (1 ml) was added via syringe and the bottle was purged with CO five times by pressurizing it to 54 psi and then releasing the pressure. Finally the reactor was pressurized to a room temperature pressure of 54 psi of CO and immersed in an oil bath at 130° C. overnight without stirring. After cooling to room temperature, pressure had decreased by 14 psi which indicates that 0.02 moles of acetic acid were formed. The beads were filtered off and and the infrared spectrum of the mother liquor showed the presence of a broad absorption band for carbonyl (>C═O) stretch of esters and carboxylic acids at around 1750 cm$^{-1}$. This characteristic infrared band for carbonyl groups and the characteristic odor of acetic acid provide evidence that the pressure decrease is due to methanol carbonylation. The infrared spectrum of the recovered catalyst was similar to that of the starting material.

EXAMPLE 4

Carbonylation of methanol with catalyst prepared from Amberlite IRA-400 resin as the solid support A sample of Amberlite IRA-400 (chloride form) was Soxhlet extracted with a 1:4 solution of water-dioxane for 24 hours. The beads were filtered off, washed with acetone and than transferred to a 150 ml fine frit. The resin was washed with a solution composed of water (250 ml), acetone (274 ml), sodium iodide (15 g), and hydriodic acid (47%, 50 ml). Finally the beads were washed with acetone, methanol, and air-dried. The yellow resin was further Soxhlet extracted with acetone for 20 hours under argon to yield the compound:

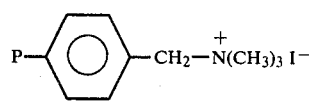

The following chemicals were loaded into a 500 ml Parr glass pressure bottle: absolute methanol (25 ml). iodomethane (2 ml), the iodide form of the Amberlite IRA-400 resin prepared above (3.1 g), and $RhCl_3.XH_2O$ (41.28% Rh; 46.8 mg). The bottle was then purged four times with CO by pressurizing it to 58 psi and then releasing the pressure. Finally the reactor was filled with CO to a room temperature pressure of 58 psi and immersed in an oil bath at 130° C. for about 21 hours. It has been shown in the homogeneous system [D. Forster, J.Am.Chem.Soc., 98, 846 (1976)] that $RhCl_3.3H_2O$ is converted to $Rh(CO)_2I_2^-$. This anion also forms in the above-described preparative method and becomes ionically bound to the Amberlite anion exchange resin to form the inventive catalyst. Cationic or neutral species would not bind. After cooling to room temperature, the pressure had decreased to 17 psi which indicates a yield if 0.02 moles of acetic acid. The red beads were filtered off, and the light yellow mother liquor was contacted with Amberlite IRA-400 resin (acetate form) during which the acetate beads changed color from tan to reddish. This color is due largely to $I_3^-$ ion. After filtration the mother liquor was colorless. If any traces of rhodium species are present in the mother liquor, they are reconverted to catalyst by ion exchange. The commercially available resin Dowex 1-X8 having the formula shown above was also used successfully in this example.

EXAMPLE 5

Preparation of catalyst using Amberlite IRA-400 (iodide and acetate forms) as the solid support and methanol carbonylation therewith The following chemicals were loaded into a 500 ml Parr glass pressure bottle: methanol (25 ml), iodomethane (2 ml), Amberlite resin (iodide form; 3.1 g), Amberlite resin (acetate form; 0.5 g), and $RhCl_3.XH_2O$ (41.28% Rh; 51.5 mg). After purging with CO as in Example 5, the bottle was filled with CO to a room temperature pressure of 56 psi, and then immersed in an oil bath at 130° C. for 23 hours. After cooling to room temperature, the pressure had decreased to 18 psi indicating a yield of 0.02 moles of acetic acid. The dark beads were collected by suction, washed with methanol, and air-dried.

EXAMPLE 6

Carbonylation of methanol using the heterogeneous catalysts generated in Examples 4 and 5

The beads generated in Examples 4 and 5 were combined and reused. They were loaded into a 500 ml Parr glass pressure bottle together with methanol (25 ml) and iodomethane (2.2 ml). The bottle was purged with CO as above and then filled with CO to a room temperature pressure of 56 psi. The reactor was immersed in an oil bath at 130° C. for 23 hours. After cooling to room temperature, the pressure had decreased by 39 psi indicating a 0.05 molar yield of acetic acid. This yield indicates that doubling the amount of catalyst doubles the rate. The beads were filtered off and to the orange mother liquor was added Amberlite IRA-400 (chloride form; 1.0 g) with stirring. After ten minutes, the mixture was filtered and the mother liquor was nearly colorless. The resin used to decolorize the mother liquor was used in the manner described in this example as a catalyst. No loss of pressure occurred after 23 hours of reaction time at 130° C. This result indicates that little or no rhodium species was present in the mother liquor.

EXAMPLE 7

Catalytic carbonylation of methanol using the catalyst of Example 6

The following chemicals were loaded into a 500 ml Parr glass pressure bottle: methanol (25 ml), iodomethane (0.5 ml), and the catalyst beads used in Example 6. After purging in the usual way, the bottle was pressurized to a room temperature of 59 psi and then heated at 130° C. in an oil bath for 24 hours. After cooling to room temperature, the pressure decreased by 11 psi indicating a yield of 0.01 moles of acetic acid. The decreased activity relative to Example 6 is attributed to the decreased iodomethane concentration. The solution process is first order in iodomethane.

EXAMPLE 8

Carbonylation of methanol using Amberlite IRA-400 (iodide form) as the catalyst solid support The following chemicals were loaded into a 500 ml Parr glass pressure bottle: absolute methanol (25 ml), iodomethane (2 ml), Amberlite IRA-400 (iodide form; 9.3 g), and $RhCl_3.XH_2O$ (41.28% Rh; 45.8 mg). In this experiment the effect of stirring was investigated. The reactor was purged with CO, pressurized with CO to a room temperature pressure of 57 psi, immersed in an oil bath at 130° C. for 20 hours, and magnetically stirred. After cooling to room temperature the pressure had decreased to 43 psi indicating a yield of 0.05 moles of acetic acid. All subsequent runs were stirred.

EXAMPLE 9

Comparison of homogeneous catalyst with heterogeneous catalyst supported on Amberlite IRA-400 (iodide form)

Homogeneous system.

The following chemicals were loaded into a 500 ml Parr glass pressure bottle: methanol (25 ml), iodomethane (1.0 ml), and $RhCl_3.XH_2O$ (41.28% Rh; 49.5 mg). The reactor was purged with CO and then pressurized with CO to a room temperature pressure of 55 psi. The system was stirred in the oil bath at a temperature of 130° C. for 14 hours. After cooling to room temperature, the pressure had decreased by 4 psi indicating a yield of 0.005 moles of acetic acid.

Heterogeneous system.

The following chemicals were loaded into a 500 ml Parr glass pressure bottle: methanol (25 ml), iodomethane (1.0 ml), $RhCl_3.XH_2O$ (41.23% Rh; 48.6 mg), and the Amberlite resin (iodide form; 2.1 g). The reactor was purged with CO and then pressurized with CO to a room temperatue pressure of 55 psi. The system was stirred in the oil bath at a temperature of 130° C. for 15 hours. After cooling to room temperature, the pressure had decreased by 11 psi indicating a yield of 0.01 moles of acetic acid. With the methyl iodide promoter the heterogeneous catalyst is three times more effective than the homogeneous analogue at this temperature in pure methanol.

EXAMPLE 10

Preparation of catalyst using Bio-Rex 9 (chloride form) as the solid support

Bio-Rex resin 9 has the formula

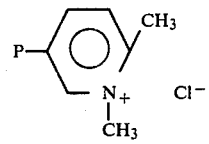

where P represents polystyrene. The following chemicals were loaded into a 500 ml Parr glass pressure bottle: glacial acetic acid (30 ml), methanol (20 ml), aqueous HI (47%; 40 g), $RhCl_3.XH_2O$ (41.28% Rh; 0.1017 g), and the Bio-Rex 9 resin (5.0 g). The reaction mixture was stirred magnetically and purged five times with CO. The pressure of CO in the bottle was increased to 60 psi at room temperature, and the reaction mixture was heated to 130° C. The system was cooled and left at room temperature for 24 hours. The pressure in the bottle was then increased to 140 psi to check for leaks, and then lowered to 95 psi after which the bottle was heated to 120° C. in the oil bath for 1½ hours. After cooling to room temperature, the pressure had dropped by 15 psi indicating a yield of 0.02 moles of acetic acid.

The beads from this reaction were filtered off and set aside. The mother liquor was stirred with fresh Bio-Rex 9 (chloride form; 5.0 g) and filtered. The purpose of this experiment was to check for the presence of Rh in both the new batch of beads and the mother liquor by running two separate carbonylation reactions.

The Bio-Rex resin that had been stirred with the mother liquor was loaded into a 500 ml Parr pressure bottle with glacial acetic acid (30 ml), methanol (20 ml), and aqueous HI (47%; 40 g). After purging the system, the bottle was pressurized with CO to a room temperature pressure of 60 psi, and heated with stirring to 120° C. for 3 hours. After cooling to room temperature, no pressure loss was observed.

The mother liquor which had been stirred with fresh Bio-Rex resin was evaporated to a small volume and loaded into the Parr bottle together with the chemicals and under the reaction conditions set forth in the preceding paragraph. No CO pressure loss was observed. It is clear that neither the mother liquor nor the beads used to extract all of the color from the mother liquor contained significant amounts of rhodium catalyst.

EXAMPLE 11

Catalytic carbonylation of methanol using a homogeneous Rh system

The following chemicals were loaded into a 500 ml Parr glass pressure bottle: a solution of pyridine (1 ml) and iodomethane (1 ml) in a few mls of methanol (allowed to stand overnight), glacial acetic acid (30 ml), methanol (30 ml), aqueous HI (47%; 50 g), and RhCl$_3$.XH$_2$O (41.28% Rh; 0.1 g). The solution was stirred and purged five times by pressurizing to 162 psi CO and releasing the pressure. The bottle was then checked for leaks by pressurizing to 162 psi for ½ hour. The pressure in the bottle was lowered to 60 psi and the bottle was immersed in an oil bath at 120° C. The loss of pressure was monitored every ½ hour and an average loss of 22 psi for each ½ hour was recorded, indicating a yield of 0.028 moles of acetic acid.

EXAMPLE 12

Investigation of rhodium species in solution at elevated temperature using an HI promoter The following chemicals were loaded into a 500 ml Parr glass pressure bottle: acetic acid (60 ml), methanol (60 ml), aqueous HI (47%; 50 g), Bio-Rex 9 resin (chloride form; 5.0 g), and RhCl$_3$.XH$_2$O (41.27% Rh; 0.2011 g). The bottle was designed to enable filtration of the solution at 120° C. and 160 psi total bottle pressure directly into another bottle which is purged with argon and cooled to −78° C. in a dry ice-acetone bath. After purging the bottle with CO, the reactor was filled to a room temperature pressure of 60 psi CO and heated in an oil bath at 120° C. The bottle was left open to the main tank of CO for three hours at 162 psi after the reaction became catalytic. After that time, 100 ml of the reaction liquid was filtered off at 120° C. and 160 psi and iodomethane (2 ml) was added. This homogeneous system was then started by filling the bottle to 60 psi CO and heating to 120° C. After the reaction became catalytic, a maximum loss of 10 psi pressure was recorded per ½ hour for a yield of 0.01 moles of acetic acid and indicating that rhodium is present in solution.

The beads in the remaining solution which was not drained at 120° C. and 160 psi were left stirring overnight after which time they were collected by suction, washed with methanol and air-dried. The mother liquor was contacted with Bio-Rex 9 resin (chloride form; 5.0 g) for one hour with stirring. The mixture was filtered leading to a colorless solution and reddish beads.

EXAMPLE 13

Investigation of rhodium in solution during the carbonylation of methanol using methyl iodide as a promoter and an excess of Bio-Rex 9 resin beads (chloride form)

The original catalyst batch from Example 12 plus the beads from the mother liquor extraction in Example 12 were loaded into a 500 ml Parr pressure bottle with methanol (60 ml), glacial acetic acid (60 ml), H$_2$O (25 ml), and iodomethane (10 ml). This produced a 1:1 proportion of rhodium substituted and unsubstituted beads. The system was purged and pressurized with CO as in Example 12. Maximum loss of CO pressure per hour was 38 psi indicating a yield of 0.05 moles of acetic acid. The bottle was rigid for filtration at high temperature and pressure into another bottle containing solid iodomethane (5 ml) at −78° C. After 100 ml of mother liquor were drained, the homogeneous carbonylation reaction was initiated with this solution.

A total of 7 psi CO pressure loss was recorded in one hour indicating a yield of 0.01 moles of acetic acid. Even with additional iodomethane promoter in this system, the decreased rate relative to Example 12 indicates that conditions can be found to minimize or completely prevent rhodium leaching.

The results recorded above indicate that the heterogeneous anionic catalysts of this invention are highly effective carbonylation catalysts. The experiments described illustrate that complete recovery of the rhodium and separation of the products from the catalyst are easily accomplished. Although batch experiments were described, it is contemplated that the catalysts can be used advantageously in a flow system. For example, in Example 6 doubling the amount of catalyst doubled the rate of CO uptake. Therefore, in a flow process where large concentrations of catalyst relative to liquid can be maintained, very rapid reaction rates can be achieved. Thus, the process could be carried out at lower temperatures under less corrosive conditions relative to processes using conventional homogeneous catalysts.

It is also contemplated that the catalysts of this invention can be used in vapor phase carbonylation processes. The catalysts described herein have all of the properties needed to be effective in this mode. Leaching would be totally eliminated in the vapor phase process, and the disclosed catalyst preparation procedure ensures that nearly all of the transition metal will be present in the catalystically active species.

This invention has been disclosed with particular reference to certain preferred embodiments thereof, but it is understood that variations and modifications can be effected within the spirit and scope of the appended claims. It is intended that all material contained in the above examples and description shall be interpreted in an illustrative and not in a limiting sense.

What is claimed is:

1. In a process for the catalytic hydroformylation of an olefin to produce the corresponding aldehyde or alcohol which comprises the reaction of an olefinic compound with carbon monoxide and hydrogen at elevated temperatures and pressures in the presence of a transition metal-containing catalyst, the improvement which comprises employing as said catalyst a heterogeneous anionic transition metal catalyst containing a catalytically effective amount of an anionic species having the formula $$M_n(CO)_m(X)_p{}^{z-}$$

where M is selected from the transition metal block consisting of rhodium, cobalt, ruthenium, osmium, iridium, and iron; X is an anionic ligand selected from the group consisting of halide, hydride, and alkyl; n ranges from 1 to 12; m ranges from 1 to 34; p ranges from 0 to 2n+1 with the proviso that when n is 1, p is at least 1; and z integer charge ranging from 1 to 5; said anionic species being ionically bound to an insoluble crosslinked anion exchange resin containing a bound quaternary ammonium cation.

2. The process of claim 1, wherein the quaternary ammonium cation is a pyridinium cation bound to a polystyrene backbone, said anion exchange resin having the formula

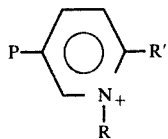

where P represents the polystyrene backbone; and R and R' are hydrogen or a lower alkyl group.

3. The process of claim 1, wherein the anion exchange resin has the formula

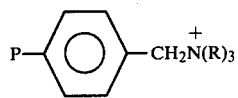

where P is a polystyrene backbone; and R is a lower alkyl group.

4. The process of claim 1, wherein the anionic species is $[Rh(CO)_2IX]^-$ where X is Cl or I.

5. The process of claim 2, wherein the anionic species is $[Rh(CO)_2IX]^-$ where X is Cl or I, and where the R and R' substituents are each methyl.

6. The process of claim 3, wherein the anionic species is $[Rh(CO)_2IX]^-$ where X is Cl or I, and where R is methyl.

* * * * *

UNITED STATES PATENT AND TRADEMARK OFFICE
CERTIFICATE OF CORRECTION

PATENT NO. : 4,417,077
DATED : November 22, 1983
INVENTOR(S) : Russell S. Drago and Anton El A'mma It is certified that error appears in the above—identified patent and that said Letters Patent is hereby corrected as shown below:

Column 2, line 49, delete "1-X3", and insert --1-X8--

Column 4, line 17, delete "(274 ml)", and insert --(275 ml)--

Column 6, line 10, delete "(41.23%", and insert --(41.28%--

Signed and Sealed this

Twenty-eighth Day of February 1984

[SEAL]

Attest:

GERALD J. MOSSINGHOFF

Attesting Officer

Commissioner of Patents and Trademarks